(12) United States Patent
Zong et al.

(10) Patent No.: US 12,626,467 B2
(45) Date of Patent: May 12, 2026

(54) REMOTE MEDICAL GUIDANCE METHOD AND SYSTEM BASED ON VIRTUAL REALITY

(71) Applicants: ARMY MEDICAL UNIVERSITY, PEOPLE'S LIBERATION ARMY, PRC, Chongqing (CN); CHONGQING UNIVERSITY OF TECHNOLOGY, Chongqing (CN)

(72) Inventors: Zhaowen Zong, Chongqing (CN); Hai Nan, Chongqing (CN); Wenjuan Du, Chongqing (CN); Renqing Jiang, Chongqing (CN); Yijun Jia, Chongqing (CN); Can Chen, Chongqing (CN); Xin Zhong, Chongqing (CN); Junting Cai, Chongqing (CN); Ye Wei, Chongqing (CN); Haoyang Yang, Chongqing (CN); Chenglin Dai, Chongqing (CN); Hao Li, Chongqing (CN)

(73) Assignees: ARMY MEDICAL UNIVERSITY PEOPLE'S LIBERATION ARMY, PRC, Chongqing (CN); CHONGQING UNIVERSITY OF TECHNOLOGY, Chongqing (CN)

( * ) Notice: Subject to any disclaimer, the term of this patent is extended or adjusted under 35 U.S.C. 154(b) by 89 days.

(21) Appl. No.: 18/603,972

(22) Filed: Mar. 13, 2024

(65) Prior Publication Data

US 2025/0209749 A1 Jun. 26, 2025

(30) Foreign Application Priority Data

Dec. 20, 2023 (CN) .......................... 202311766441.8

(51) Int. Cl.
*G06T 19/00* (2011.01)
*A61B 34/10* (2016.01)
(Continued)

(52) U.S. Cl.
CPC ............ *G06T 19/006* (2013.01); *A61B 34/10* (2016.02); *A61B 90/37* (2016.02); *G06T 7/73* (2017.01);
(Continued)

(58) Field of Classification Search
None
See application file for complete search history.

(56) References Cited

U.S. PATENT DOCUMENTS 8,253,779 B2 * 8/2012 Stetten ................... A61B 8/587
348/45
2020/0246084 A1 * 8/2020 Azizian .................. A61B 90/37
(Continued)

*Primary Examiner* — David H Chu
(74) *Attorney, Agent, or Firm* — Mark C. Johnson; Johnson |Dalal

(57) ABSTRACT

Disclosed are a remote medical guidance method and system based on virtual reality, belonging to the technical field of medical guidance. The method includes: obtaining an action sequence of remote guidance personnel for medical operations; and generating a three-dimensional operation model based on the action sequence and displaying the three-dimensional operation model in an operation live scene. The present disclosure achieves remote guidance of medical operations based on virtual reality, eliminating the need to relocate patients or medical personnel and avoiding missing the optimal treatment time window.

8 Claims, 3 Drawing Sheets

Obtain an action sequence of remote guidance personnel for medical operations — Step 101

Generate a three-dimensional operation model based on the action sequence, and display the three-dimensional operation model in an operation live scene — Step 102

(51) Int. Cl.

| | |
|---|---|
| *A61B 90/00* | (2016.01) |
| *G06T 7/73* | (2017.01) |
| *G06V 10/44* | (2022.01) |
| *G06V 40/10* | (2022.01) |
| *G09B 5/02* | (2006.01) |

(52) U.S. Cl.
CPC .............. *G06V 10/44* (2022.01); *G06V 40/11* (2022.01); *G09B 5/02* (2013.01); *A61B 2034/105* (2016.02); *A61B 2090/365* (2016.02); *G06T 2207/10024* (2013.01); *G06T 2207/10028* (2013.01); *G06T 2207/30004* (2013.01); *G06T 2207/30196* (2013.01); *G06T 2210/41* (2013.01); *G06V 2201/03* (2022.01)

(56) References Cited

U.S. PATENT DOCUMENTS

| | | | |
|---|---|---|---|
| 2021/0049824 A1* | 2/2021 | Edwards ............... | G02B 27/017 |
| 2022/0122327 A1* | 4/2022 | Bilgory ................. | G06V 20/20 |
| 2022/0293014 A1* | 9/2022 | Fisher .................. | G09B 23/285 |
| 2022/0310253 A1* | 9/2022 | Ferro, Jr. ............. | G06T 19/006 |
| 2024/0024065 A1* | 1/2024 | Okumu .................. | G06V 20/50 |
| 2025/0134610 A1* | 5/2025 | Murugappan .......... | A61B 34/25 |
| 2025/0248771 A1* | 8/2025 | Jarc ....................... | A61B 34/25 |

* cited by examiner

Remote terminal

RGB camera
Depth camera
Data processing
module

On-site medical
terminal

AR device

FIG. 6

REMOTE MEDICAL GUIDANCE METHOD AND SYSTEM BASED ON VIRTUAL REALITY

CROSS-REFERENCE TO RELATED APPLICATIONS

This patent application claims the benefit and priority of Chinese Patent Application No. 2023117664418, filed with the China National Intellectual Property Administration on Dec. 20, 2023, the disclosure of which is incorporated by reference herein in its entirety as part of the present application.

TECHNICAL FIELD

The present disclosure relates to the technical field of medical guidance, and in particular, to a remote medical guidance method and system based on virtual reality.

BACKGROUND

In the field of healthcare, in the case of complex surgeries or emergency procedures that on-site medical personnel cannot handle, the usual approach is to either transfer the patient or bring personnel capable of performing the operation to the site. However, this method is time-consuming and labor-intensive, and may result in missing the optimal treatment time window.

SUMMARY

An objective of the present disclosure is to provide a remote medical guidance method and system based on virtual reality to achieve remote guidance without relocating patients or medical personnel.

To achieve the above objective, the present disclosure provides the following technical solutions.

The present disclosure provides a remote medical guidance method based on virtual reality, including the following steps:

obtaining an action sequence of remote guidance personnel for medical operations; and generating a three-dimensional operation model based on the action sequence and displaying the three-dimensional operation model in an operation live scene.

The present disclosure further provides a remote medical guidance system based on virtual reality. The system includes a remote terminal and an on-site medical terminal. The on-site medical terminal includes an augmented reality (AR) device worn by medical personnel.

The remote terminal and the on-site medical terminal are connected.

The remote terminal is configured to obtain an action sequence of remote guidance personnel for medical operations.

The on-site medical terminal is configured to generate a three-dimensional operation model based on the action sequence and display the three-dimensional operation model in an operation live scene.

According to specific embodiments provided in the present disclosure, the present disclosure has the following technical effects:

Embodiments of the present disclosure provide a remote medical guidance method and system based on virtual reality. The method includes: obtaining an action sequence of remote guidance personnel for medical operations; and generating a three-dimensional operation model based on the action sequence and displaying the three-dimensional operation model in an operation live scene. The present disclosure achieves remote guidance of medical operations based on virtual reality, eliminating the need to relocate patients or medical personnel and avoiding missing the optimal treatment time window.

BRIEF DESCRIPTION OF THE DRAWINGS

To describe the technical solutions in embodiments of the present disclosure or in the prior art more clearly, the accompanying drawings required in the embodiments are briefly described below. Apparently, the accompanying drawings in the following description show merely some embodiments of the present disclosure, and other drawings can be derived from these accompanying drawings by those of ordinary skill in the art without creative efforts.

FIG. 6 is a schematic structural diagram of a remote medical guidance system based on virtual reality according to an embodiment of the present disclosure.

DETAILED DESCRIPTION OF THE EMBODIMENTS

The technical solutions in the embodiments of the present disclosure are described clearly and completely below with reference to the accompanying drawings in the embodiments of the present disclosure. Apparently, the described embodiments are merely some rather than all of the embodiments of the present disclosure. All other embodiments obtained by those skilled in the art based on the embodiments of the present disclosure without creative efforts shall fall within the protection scope of the present disclosure.

An objective of the present disclosure is to provide a remote medical guidance method and system based on virtual reality to achieve remote guidance without relocating patients or medical personnel.

In order to make the above objective, features and advantages of the present disclosure clearer and more comprehensible, the present disclosure will be further described in detail below in combination with accompanying drawings and particular implementation modes.

Figure 1:
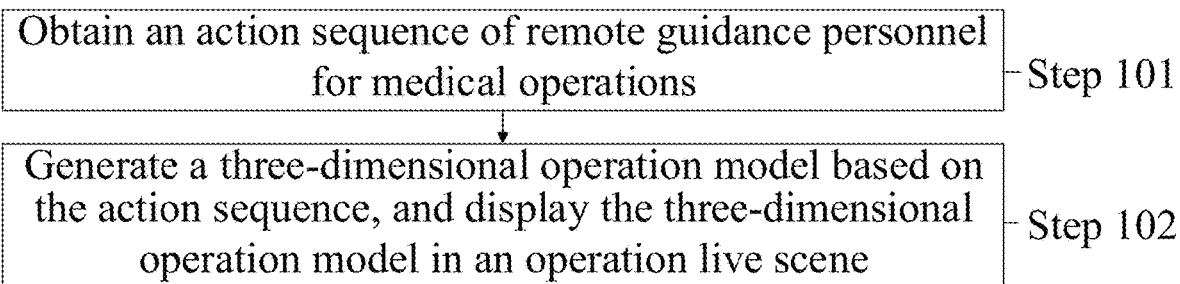
FIG. 1 is a flowchart of a remote medical guidance method based on virtual reality according to an embodiment of the present disclosure.

An embodiment of the present disclosure provides a remote medical guidance method based on virtual reality. As shown in FIG. 1, the method includes the following steps:

In step 101, an action sequence of remote guidance personnel for medical operations is obtained.

In step 102, a three-dimensional operation model is generated based on the action sequence, and the three-dimensional operation model is displayed in an operation live scene.

In this embodiment of the present disclosure, the transmitted action sequence is in a data form, which, compared to image transmission, has a higher transmission rate, improving the real-time performance of data transmission.

For example, the action sequence in this embodiment of the present disclosure is a sequence of three-dimensional coordinates of key points at each moment. Specifically, said obtaining the action sequence of the remote guidance personnel for the medical operations includes: obtaining RGB images at each moment during a medical operation process by the remote guidance personnel; obtaining depth images at each moment during the medical operation process by the remote guidance personnel; processing the RGB images at each moment to obtain plane position coordinates of the key points at different moments, where the key points are hand joints of the remote guidance personnel; processing the depth images at each moment to obtain depth position coordinates of the key points at different moments; and generating the action sequence based on the plane position coordinates and the depth position coordinates of the key points at different moments.

In this embodiment of the present disclosure, the three-dimensional coordinates of the key points are obtained based on the RGB images and the depth images. Compared to the approach that directly uses depth images, the technology of processing RGB images is more mature, with higher timeliness and accuracy. For example, said processing the RGB images at each moment to obtain the plane position coordinates of the key points at different moments includes: extracting a region of interest from the RGB images, where the region of interest is an area in which hands of the remote guidance personnel are located; performing edge recognition on the region of interest to obtain a hand contour; based on the hand contour and a hand skeletal structure, identifying the hand joints as the key points; determining position information of the identified key points in the RGB images; and performing coordinate transformation on the position information of the key points in the RGB images to determine the plane position coordinates of the key points, where the plane position coordinates include x-axis coordinates and y-axis coordinates in a world coordinate system.

Said processing the depth images at each moment to obtain the depth position coordinates of the key points at different moments includes: aligning the depth image with the RGB image at the same moment based on intrinsic parameters and extrinsic parameters of an RGB camera and a depth camera to obtain aligned depth images; based on position information of the key points in the RGB images, determining depth information of the key points at corresponding positions in the aligned depth images; and performing coordinate transformation on the depth information of the key points at the corresponding positions in the aligned depth images to determine the depth position coordinates of the key points, where the depth position coordinates are z-axis coordinates in the world coordinate system.

It can be seen that in this embodiment of the present disclosure, in the process of obtaining the depth information based on the depth images, it is unnecessary to perform image recognition on the depth images, and the corresponding key points can be found by aligning the depth images with the RGB images, to obtain depth information.

For example, said generating the three-dimensional operation model based on the action sequence is specifically as follows:

The key points at each moment are located, connected, and rendered based on the plane position coordinates and the depth position coordinates of the key points at each moment, to generate three-dimensional hand pose models for each moment. The positioning, connecting, and rendering in the embodiments of the present disclosure can be performed in 3D software. The rendering can be direct rendering based on the software or rendering based on hand image information, which is not limited in the embodiments of the present disclosure.

The three-dimensional hand pose models for each moment are arranged and connected in chronological order to generate the three-dimensional operation model.

The coordinate transformations involved in the embodiments of the present disclosure use coordinate transformation techniques, which are specifically as follows:

1. Image Coordinate System

Figure 2:
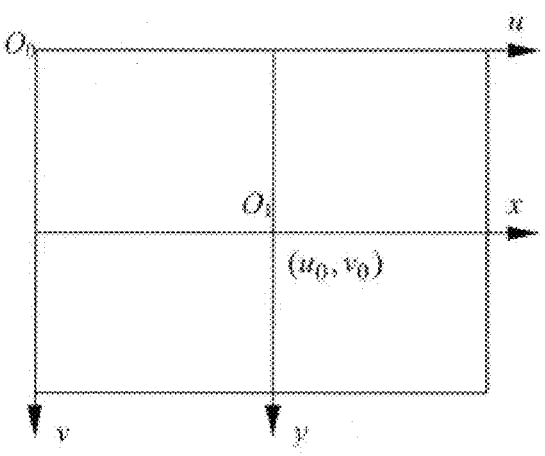
FIG. 2 is a schematic diagram of an image coordinate system according to an embodiment of the present disclosure.

As shown in FIG. 2, a direct coordinate system u-v in pixels is established with the top-left corner of the image as the origin. The horizontal coordinate u and the vertical coordinate v correspond to a column number and a row number in an image array (in OpenCV, u corresponds to x, and v corresponds to y).

(u, v) only represents the column number and the row number of pixels, while the position of the pixel in the image is not represented in physical units. Therefore, an image coordinate system x-y in physical units (such as millimeters) needs to be established. An intersection point of an optical axis of a camera with an image plane (which is generally located at the center of the image plane, also known as the principal point) is defined as the origin $O_1$ of this coordinate system. The x-axis is parallel to the u-axis, and the y-axis is parallel to the v-axis. Assuming that $(u_0, v_0)$ represents the coordinates of $O_1$ in the u-v coordinate system, and dx and dy represent physical dimensions of each pixel on the x-axis and y-axis, respectively, the relationship between the coordinates of each pixel in the u-v coordinate system and the x-y coordinate system is given by the following formula:

$$u = \frac{x}{dx} + u_0 \tag{1}$$
$$v = \frac{y}{dy} + v_0$$

In the above formula, assuming that the unit in the physical coordinate system is millimeters, the unit of dx is millimeters/pixel. Therefore, the unit of x/dx is pixels, which is the same as the unit of u.

For convenience, the above relationship can be expressed in homogeneous coordinates and matrix form as follows:

$$\begin{bmatrix} u \\ v \\ 1 \end{bmatrix} = \begin{bmatrix} \dfrac{1}{dx} & 0 & u_0 \\ 0 & \dfrac{1}{dy} & v_0 \\ 0 & 0 & 1 \end{bmatrix} \begin{bmatrix} x \\ y \\ 1 \end{bmatrix} \tag{2}$$

An inverse relationship thereof can be expressed as follows:

$$\begin{bmatrix} x \\ y \\ 1 \end{bmatrix} = \begin{bmatrix} dx & 0 & -u_0 dx \\ 0 & dy & -v_0 dy \\ 0 & 0 & 1 \end{bmatrix} \begin{bmatrix} u \\ v \\ 1 \end{bmatrix} \tag{3}$$

2. Camera Coordinate System

Figure 3:
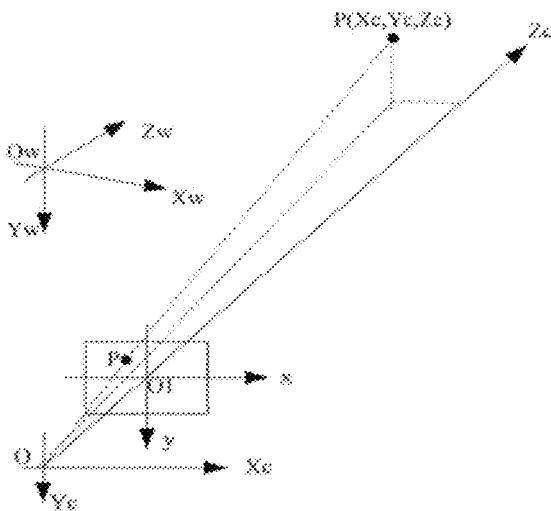
FIG. 3 is a schematic diagram of a camera coordinate system and a world coordinate system according to an embodiment of the present disclosure.

A geometric relationship of camera imaging is illustrated in FIG. 3. O represents an optical center of the camera (center of projection), Xc-axis and Yc-axis are parallel to the x-axis and y-axis of the coordinate system of the image plane, and Zc-axis is the optical axis of the camera, which is perpendicular to the image plane. The intersection point of the optical axis with the image plane is the principal point O1 of the image. The right-angled coordinate system formed by the point O with the Xc-axis, Yc-axis, and Zc-axis is referred to as the camera coordinate system, and OO1 represents a focal length of the camera.

3. World Coordinate System

The world coordinate system is introduced to describe the position of the camera. As shown in FIG. 3, the coordinate system formed by Ow, Xw, Yw, and Zw represents the world coordinate system. The translation vector t and the rotation matrix R can be used to represent the relationship between the camera coordinate system and the world coordinate system. Therefore, assuming that the homogeneous coordinates of a spatial point P in the world coordinate system are $(X_w, Y_w, Z_w, 1)$ T (where T is a superscript denoting a transpose operation) and in the camera coordinate system are $(X_c, Y_c, Z_c, 1)$ T, the following relationship exists:

$$\begin{bmatrix} X_c \\ Y_c \\ Z_c \end{bmatrix} = \begin{bmatrix} R & t \\ \overline{0} & 1 \end{bmatrix} \begin{bmatrix} X_w \\ Y_w \\ Z_w \\ 1 \end{bmatrix} = M_1 \begin{bmatrix} X_w \\ Y_w \\ Z_w \\ 1 \end{bmatrix} \tag{4}$$

In the above equation, R is a 3×3 orthogonal unit matrix (also called a rotation matrix), t is a three-dimensional translation vector, the vector $0=(0, 0, 0)$, and $M_1$ is a 4×4 matrix.

Figure 4:
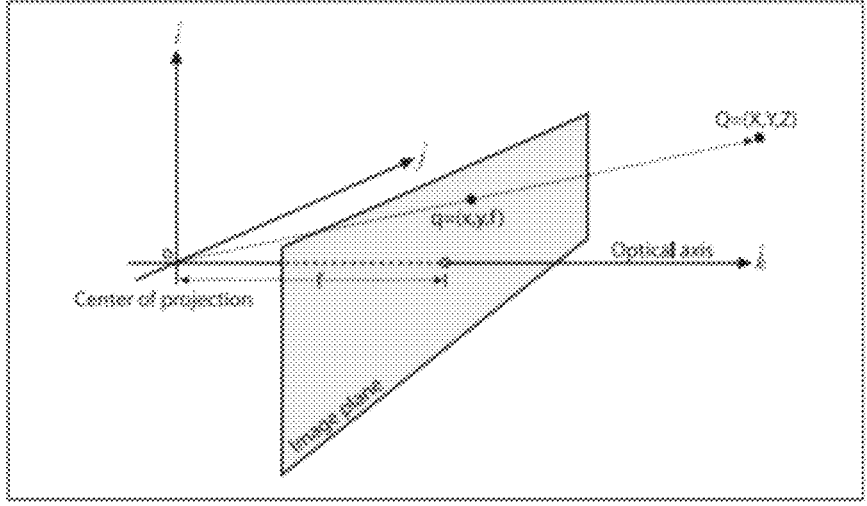
FIG. 4 is a schematic diagram showing a relationship between the image coordinate system and the camera coordinate system according to an embodiment of the present disclosure.

4. Relationship Between the Image Coordinate System and the Camera Coordinate System As shown in FIG. 4, the actual plane coordinate system of the image plane is the image coordinate system, and the camera coordinate system is formed by the center of projection and i, j, k.

In practice, the principal point may not necessarily be at the center of the imaging device (image plane). To model the possible offset of the optical axis, two new parameters, cx and cy, are introduced.

In practice, since a single pixel has a rectangular shape instead of a square shape on a low-cost imaging device, two different focal length parameters, fx and fy, are introduced. (Here, the focal length is in pixels.)

Assuming that a point Q in the camera coordinate system with coordinates (X, Y, Z) is projected with an offset to a point q $(X_{srceen}, Y_{scrreen})$, where screen is the subscript, the coordinate relationship is as follows:

$$x_{screen} = f_x \left( \frac{X}{Z} \right) + c_x, \quad y_{screen} = f_y \left( \frac{Y}{Z} \right) + c_y \tag{5}$$

The relationships of fx and fy with respect to the physical focal length F are as follows: $f_x = F_{sx}$ and $f_y = F_{sy}$. $s_x$ denotes a pixel value that represents 1 millimeter in the x direction, i.e., pixels per millimeter; $f_x$ and $f_y$ are calculated as a whole in camera calibration.

Figure 5:
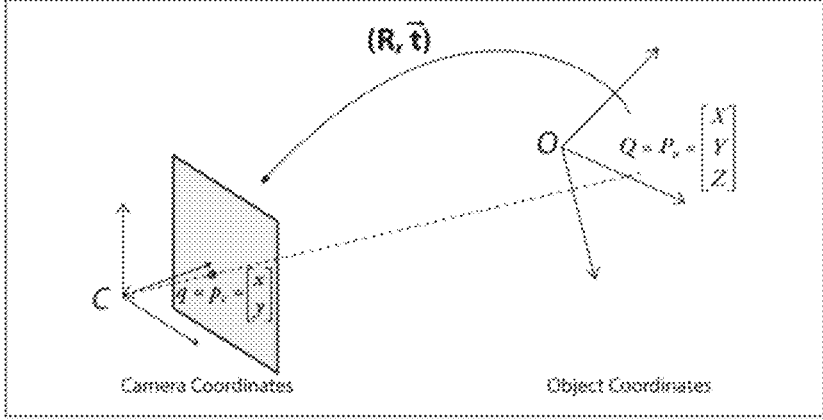
FIG. 5 is a schematic diagram showing a relationship between the camera coordinate system and the world coordinate system according to an embodiment of the present disclosure.

5. Relationship Between the Camera Coordinate System and the World Coordinate System As shown in FIG. 5, as for the rotation matrix R, typically, any-dimensional rotation can be represented as a product of a coordinate vector and a square matrix of appropriate dimensions. Finally, a rotation is equivalent to a re-description of the position of a point in another coordinate system. If a coordinate system is rotated by an angle θ, it is equivalent to rotating a target point in the opposite direction by the same angle θ around the origin. The following formula demonstrates the description of 2D rotation through matrix multiplication. In a three-dimensional space, rotation can be decomposed into two-dimensional rotations around respective coordinate axes. The measurement of the axis of rotation remains unchanged (which is why the rotation matrix is an orthogonal matrix). In the case of rotations around x, y, and z axes by angles ψ, φ, and θ successively, an overall rotation matrix R is a product of three matrices $R_x(ψ)$, $R_y(φ)$, and $R_z(θ)$.

$$R_x(\psi) = \begin{bmatrix} 1 & 0 & 0 \\ 0 & \cos\psi & \sin\psi \\ 0 & -\sin\psi & \cos\psi \end{bmatrix} \tag{6}$$

$$R_y(\varphi) = \begin{bmatrix} \cos\varphi & 0 & -\sin\varphi \\ 0 & 1 & 0 \\ \sin\varphi & 0 & \cos\varphi \end{bmatrix}$$

$$R_x(\theta) = \begin{bmatrix} \cos\theta & \sin\theta & 0 \\ -\sin\theta & \cos\theta & 0 \\ 0 & 0 & 1 \end{bmatrix}$$

Thus, $R=R_x(ψ)$, $R_y(φ)$, $R_z(θ)$.

As for the translation vector T, the translation vector is used to represent how to move the origin of one coordinate system to the origin of another coordinate system or, in other words, the translation vector is an offset between the origin of the first coordinate system and the origin of the second coordinate system. Therefore, to move from a coordinate system with a target center as the origin to another coordinate system with the camera as the origin requires the corresponding translation vector T=target origin—camera origin. Then, transformation from coordinates $P_o$ of a point in the world coordinate system to coordinates Pc in the camera coordinate system is expressed as follows: $P_c = R(P_o - T)$.

Therefore, a three-dimensional rotation is represented by three angles ψ, φ, and θ, and a three-dimensional translation is represented by three parameters (x, y, z). There are a total of 6 parameters. For a camera, an internal parameter matrix of OpenCV has 4 parameters: $f_x$, $f_y$, $c_x$, $c_y$. Therefore, the solution for each viewpoint requires 10 parameters. A quadrilateral with 4 points can provide 8 equations. Therefore, at least two viewpoints are needed to solve all geometric parameters.

Figure 6:
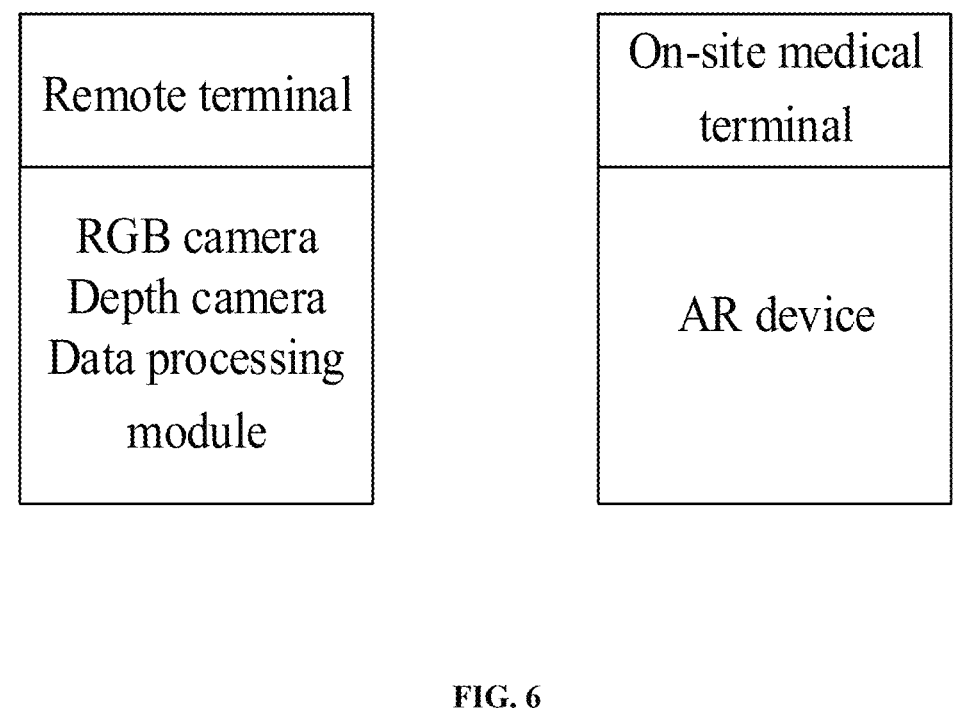

An embodiment of the present disclosure further provides a remote medical guidance system based on virtual reality. As shown in FIG. 6, the system includes a remote terminal and an on-site medical terminal. The on-site medical terminal includes an AR device worn by medical personnel. The remote terminal and the on-site medical terminal are connected. The remote terminal is configured to obtain an action sequence of remote guidance personnel for medical operations. The on-site medical terminal is configured to generate a three-dimensional operation model based on the action sequence and display the three-dimensional operation model in an operation live scene.

In the embodiments of the present disclosure, the AR device is used, which can display a virtual three-dimensional operation model in an operation live scene, simulate on-site guidance, and allow an on-site operator to directly wear the AR device to conduct on-site operations under the guidance provided through the live scene.

For example, the remote terminal includes an RGB camera, a depth camera, and a data processing module. The RGB camera is connected to the data processing module. The RGB camera is configured to obtain RGB images at each moment during a medical operation process by the remote guidance personnel. The depth camera is connected to the data processing module. The depth camera is configured to obtain depth images at each moment during the medical operation process by the remote guidance personnel. The data processing module is connected to the on-site medical terminal. The data processing module is configured to process the RGB images at each moment to obtain plane position coordinates of the key points at different moments; process the depth images at each moment to obtain depth position coordinates of the key points at different moments; and generate the action sequence based on the plane position coordinates and the depth position coordinates of the key points at different moments. The key points are hand joints of the remote guidance personnel.

In terms of processing the RGB images at each moment to obtain the plane position coordinates of the key points at different moments, the data processing module is specifically configured to extract a region of interest from the RGB images, where the region of interest is an area in which hands of the remote guidance personnel are located; perform edge recognition on the region of interest to obtain a hand contour; based on the hand contour and a hand skeletal structure, identify the hand joints as the key points; determine position information of the identified key points in the RGB images; and perform coordinate transformation on the position information of the key points in the RGB images to determine the plane position coordinates of the key points, where the plane position coordinates include x-axis coordinates and y-axis coordinates in a world coordinate system.

In terms of processing the depth images at each moment to obtain the depth position coordinates of the key points at different moments, the data processing module is specifically configured to align the depth image with the RGB image at the same moment based on intrinsic parameters and extrinsic parameters of the RGB camera and the depth camera to obtain aligned depth images; based on position information of the key points in the RGB images, determine depth information of the key points at corresponding positions in the aligned depth images; and perform coordinate transformation on the depth information of the key points at the corresponding positions in the aligned depth images to determine the depth position coordinates of the key points, where the depth position coordinates are z-axis coordinates in the world coordinate system.

In terms of generating the three-dimensional operation model based on the action sequence, the on-site medical terminal is specifically configured to locate, connect, and render the key points at each moment based on the plane position coordinates and the depth position coordinates of the key points at each moment, to generate three-dimensional hand pose models for each moment; and arrange and connect the three-dimensional hand pose models for each moment in chronological order to generate the three-dimensional operation model.

The implementations of the functions of the system in the present disclosure are consistent with the implementations of the steps in the method, and details are not described again.

To sum up, the embodiments of the present disclosure have the following beneficial effects:

Embodiments of the present disclosure provide a remote medical guidance method and system based on virtual reality. The method includes: obtaining an action sequence of remote guidance personnel for medical operations; and generating a three-dimensional operation model based on the action sequence and displaying the three-dimensional operation model in an operation live scene. The present disclosure achieves remote guidance of medical operations based on virtual reality, eliminating the need to relocate patients or medical personnel and avoiding missing the optimal treatment time window.

Each embodiment in the description is described in a progressive mode, each embodiment focuses on differences from other embodiments, and references can be made to each other for the same and similar parts between embodiments. Since the system disclosed in an embodiment corresponds to the method disclosed in an embodiment, the description is relatively simple, and for related contents, references can be made to the description of the method.

Particular examples are used herein for illustration of principles and implementation modes of the present disclosure. The descriptions of the above embodiments are merely used for assisting in understanding the method of the present disclosure and its core ideas. In addition, those of ordinary skill in the art can make various modifications in terms of particular implementation modes and the scope of application in accordance with the ideas of the present disclosure. In conclusion, the content of the description shall not be construed as limitations to the present disclosure.

What is claimed is:

1. A remote medical guidance method based on virtual reality, comprising the following steps:

obtaining an action sequence of remote guidance personnel for medical operations; and generating a three-dimensional operation model based on the action sequence and displaying the three-dimensional operation model in an operation live scene;

wherein said obtaining the action sequence of the remote guidance personnel for the medical operations specifically comprises;

obtaining RGB images at each moment during a medical operation process by the remote guidance personnel:

obtaining depth images at each moment during the medical operation process by the remote guidance personnel:

processing the RGB images at each moment to obtain plane position coordinates of key points at different moments, wherein the key points are hand joints of the remote guidance personnel:

processing the depth images at each moment to obtain depth position coordinates of the key points at different moments; and generating the action sequence based on the plane position coordinates and the depth position coordinates of the key points at different moments.

2. The remote medical guidance method based on virtual reality according to claim 1, wherein said processing the RGB images at each moment to obtain the plane position coordinates of the key points at different moments specifically comprises:

extracting a region of interest from the RGB images, wherein the region of interest is an area in which hands of the remote guidance personnel are located;

performing edge recognition on the region of interest to obtain a hand contour;

based on the hand contour and a hand skeletal structure, identifying the hand joints as the key points;

determining position information of the identified key points in the RGB images; and performing coordinate transformation on the position information of the key points in the RGB images to determine the plane position coordinates of the key points, wherein the plane position coordinates comprise x-axis coordinates and y-axis coordinates in a world coordinate system.

3. The remote medical guidance method based on virtual reality according to claim 1, wherein said processing the depth images at each moment to obtain the depth position coordinates of the key points at different moments specifically comprises:

aligning the depth image with the RGB image at the same moment based on intrinsic parameters and extrinsic parameters of an RGB camera and a depth camera to obtain aligned depth images;

based on position information of the key points in the RGB images, determining depth information of the key points at corresponding positions in the aligned depth images; and performing coordinate transformation on the depth information of the key points at the corresponding positions in the aligned depth images to determine the depth position coordinates of the key points, wherein the depth position coordinates are z-axis coordinates in a world coordinate system.

4. The remote medical guidance method based on virtual reality according to claim 1, wherein said generating the three-dimensional operation model based on the action sequence specifically comprises:

locating, connecting, and rendering the key points at each moment based on the plane position coordinates and the depth position coordinates of the key points at each moment, to generate three- dimensional hand pose models for each moment, and arranging and connecting the three-dimensional hand pose models for each moment in chronological order to generate the three-dimensional operation model.

5. A remote medical guidance system based on virtual reality, comprising a remote terminal and an on-site medical terminal, wherein the on-site medical terminal comprises an augmented reality (AR) device worn by medical personnel;

the remote terminal and the on-site medical terminal are connected;

the remote terminal is configured to obtain an action sequence of remote guidance personnel for medical operations; and the on-site medical terminal is configured to generate a three-dimensional operation model based on the action sequence and display the three-dimensional operation model in an operation live scene;

wherein the remote terminal comprises an RGB camera, a depth camera, and a data processing module:

the RGB camera is connected to the data processing module, and is configured to obtain RGB images at each moment during a medical operation process by the remote guidance personnel;

the depth camera is connected to the data processing module, and is configured to obtain depth images at each moment during the medical operation process by the remote guidance personnel; and the data processing module is connected to the on-site medical terminal, and is configured to process the RGB images at each moment to obtain plane position coordinates of the key points at different moments; process the depth images at each moment to obtain depth position coordinates of the key points at different moments; and generate the action sequence based on the plane position coordinates and the depth position coordinates of the key points at different moments, wherein the key points are hand joints of the remote guidance personnel.

6. The remote medical guidance system based on virtual reality according to claim 5, wherein in terms of processing the RGB images at each moment to obtain the plane position coordinates of the key points at different moments, the data processing module is specifically configured to:

extract a region of interest from the RGB images, wherein the region of interest is an area in which hands of the remote guidance personnel are located;

perform edge recognition on the region of interest to obtain a hand contour;

based on the hand contour and a hand skeletal structure, identify the hand joints as the key points;

determine position information of the identified key points in the RGB images; and perform coordinate transformation on the position information of the key points in the RGB images to determine the plane position coordinates of the key points, wherein the plane position coordinates comprise x-axis coordinates and y-axis coordinates in a world coordinate system.

7. The remote medical guidance system based on virtual reality according to claim 5, wherein in terms of processing the depth images at each moment to obtain the depth position coordinates of the key points at different moments, the data processing module is specifically configured to:

align the depth image with the RGB image at the same moment based on intrinsic parameters and extrinsic parameters of an RGB camera and a depth camera to obtain aligned depth images;

based on position information of the key points in the RGB images, determine depth information of the key points at corresponding positions in the aligned depth images; and perform coordinate transformation on the depth information of the key points at the corresponding positions in the aligned depth images to determine the depth position coordinates of the key points, wherein the depth position coordinates are z-axis coordinates in a world coordinate system.

8. The remote medical guidance system based on virtual reality according to claim 5, wherein in terms of generating the three-dimensional operation model based on the action sequence, the on-site medical terminal is specifically configured to:

locate, connect, and render the key points at each moment based on the plane position coordinates and the depth position coordinates of the key points at each moment, to generate three- dimensional hand pose models for each moment; and arrange and connect the three-dimensional hand pose models for each moment in chronological order to generate the three-dimensional operation model.

* * * * *